United States Patent
Wald et al.

(10) Patent No.: US 10,830,764 B2
(45) Date of Patent: Nov. 10, 2020

(54) FLUORESCENCE-BASED CHEMICAL DETECTION OF AMINE-BASED SUBSTANCES

(71) Applicant: FLIR Detection, Inc., Stillwater, OK (US)

(72) Inventors: Lara B. Wald, Stillwater, OK (US); Steven L. Keen, Stillwater, OK (US)

(73) Assignee: FLIR Detection, Inc., Stillwater, OK (US)

( * ) Notice: Subject to any disclaimer, the term of this patent is extended or adjusted under 35 U.S.C. 154(b) by 288 days.

(21) Appl. No.: 15/842,451

(22) Filed: Dec. 14, 2017

(65) Prior Publication Data

US 2018/0180599 A1 Jun. 28, 2018

Related U.S. Application Data

(60) Provisional application No. 62/439,399, filed on Dec. 27, 2016.

(51) Int. Cl.

| | |
|---|---|
| *G01N 33/00* | (2006.01) |
| *G01N 33/52* | (2006.01) |
| *G01N 33/94* | (2006.01) |
| *G01N 21/64* | (2006.01) |
| *C07D 215/04* | (2006.01) |
| *G01N 21/25* | (2006.01) |
| *G01N 31/22* | (2006.01) |

(52) U.S. Cl.
CPC .......... *G01N 33/52* (2013.01); *C07D 215/04* (2013.01); *G01N 21/255* (2013.01); *G01N 21/6428* (2013.01); *G01N 31/22* (2013.01); *G01N 33/946* (2013.01); *G01N 2021/6432* (2013.01); *G01N 2201/061* (2013.01)

(58) Field of Classification Search
CPC ...................................................... G01N 33/52
USPC ........................................................... 436/96
See application file for complete search history.

(56) References Cited

U.S. PATENT DOCUMENTS

| | | | |
|---|---|---|---|
| 6,558,626 B1 | 5/2003 | Aker et al. | |
| 7,799,573 B2 * | 9/2010 | Deans | C07D 471/14 422/52 |
| 9,005,524 B2 | 4/2015 | Deans et al. | |
| 9,068,960 B2 | 6/2015 | Wald et al. | |
| 9,448,180 B2 | 9/2016 | O'Dell et al. | |
| 9,588,091 B2 | 3/2017 | Wald et al. | |
| 2014/0106463 A1 * | 4/2014 | Wald | G01N 31/227 436/110 |
| 2015/0316483 A1 * | 11/2015 | Deans | G01N 21/76 506/12 |

\* cited by examiner

*Primary Examiner* — Christine T Mui
*Assistant Examiner* — Emily R. Berkeley
(74) *Attorney, Agent, or Firm* — Haynes and Boone, LLP

(57) ABSTRACT

Various techniques are provided to determine the presence of trace chemicals corresponding to various materials of interest. In one example, a method includes providing a chemical reporter of a chemical detector. The chemical reporter includes protonated 2-[5-methoxy-2-(4-phenyl-quinoline-2yl)-phenyl]-ethanol. A vapor-phase amine compound is subsequently received at the chemical reporter. The chemical detector then detects a response of the chemical reporter to the amine compound to determine whether materials of interest are present. Additional methods and related devices are also provided.

20 Claims, 9 Drawing Sheets

FLUORESCENCE-BASED CHEMICAL DETECTION OF AMINE-BASED SUBSTANCES

CROSS-REFERENCE TO RELATED APPLICATIONS

This application claims the benefit of and priority to U.S. Provisional Patent Application No. 62/439,399 filed Dec. 27, 2016 and entitled "FLUORESCENCE-BASED CHEMICAL DETECTION OF AMINE-BASED SUBSTANCES," which is incorporated herein by reference in its entirety.

TECHNICAL FIELD

The present invention relates generally to chemical detection and, more particularly, to the detection of trace materials of interest.

BACKGROUND

Detection of explosives, narcotics, and other materials of interest for security is an area of ongoing global concern. Concerted efforts have been focused on the detection of trace amounts of explosives and narcotics.

Conventional detection methods, such as X-ray diffraction, nuclear quadruple resonance, ion mobility spectrometry, mass spectrometry, and gas chromatography are known and are highly sensitive and effective. Systems used to carry out these methods, however, are expensive, difficult to maintain, susceptible to false positives, and are not easily manufactured into low-power, portable devices.

Calorimetric techniques are known that can detect the presence of materials of interest. Portable colorimetric chemical kits have the value of displaying interpreted optical signals with fast response times. These methods, however, have a number of disadvantages, including low sensitivity, high false alarm rates, and inconvenient analysis and clean-up procedures due to the liquid-based detection mechanisms. In addition, these methods can often expose users to large quantities of chemicals through repeated wet-chemistry style sampling steps.

SUMMARY

Various techniques are provided for the detection of trace amounts of amine-based substances. Such amine-based substances include, but are not limited to, methamphetamine, methamphetamine hydrochloride, cocaine, cocaine hydrochloride, 3,4-methylenedioxymethamphetamine (MDMA), MDMA hydrochloride, heroin, and heroin hydrochloride. Thus, the methods described herein are not only responsive to amine-based substances in the free-base form, but also their hydrochloride salts, which have substantially lower vapor pressures.

In various embodiments, protonated 2-[5-methoxy-2-(4-phenyl-quinoline-2yl)-phenyl]-ethanol (PQP) is provided that facilitates the detection of certain amine-based substances at a chemical reporter upon interaction of the protonated PQP with an amine-based substance. The protonated PQP is fluorescent. Exposure of the protonated PQP to an amine-based substance deprotonates the protonated PQP, resulting in a change in fluorescence. In some embodiments, reaction of the amine-based substance with the protonated PQP quenches the emission of the protonated PQP or decreases the fluorescent response intensity.

In one embodiment, a method includes providing a chemical reporter of a chemical detector, the chemical reporter comprising protonated PQP; receiving a vapor-phase amine compound at the chemical reporter; and detecting, by the chemical detector, a response of the chemical reporter to the amine compound to determine whether materials of interest are present.

In another embodiment, a device includes an inlet configured to receive a vapor-phase amine compound; and a chemical detector comprising a chemical reporter configured to respond to the amine compound, wherein the chemical reporter comprises a combination of PQP and a non-volatile acid, and is configured to detect a response of the chemical reporter to the amine compound to determine whether materials of interest are present.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1:
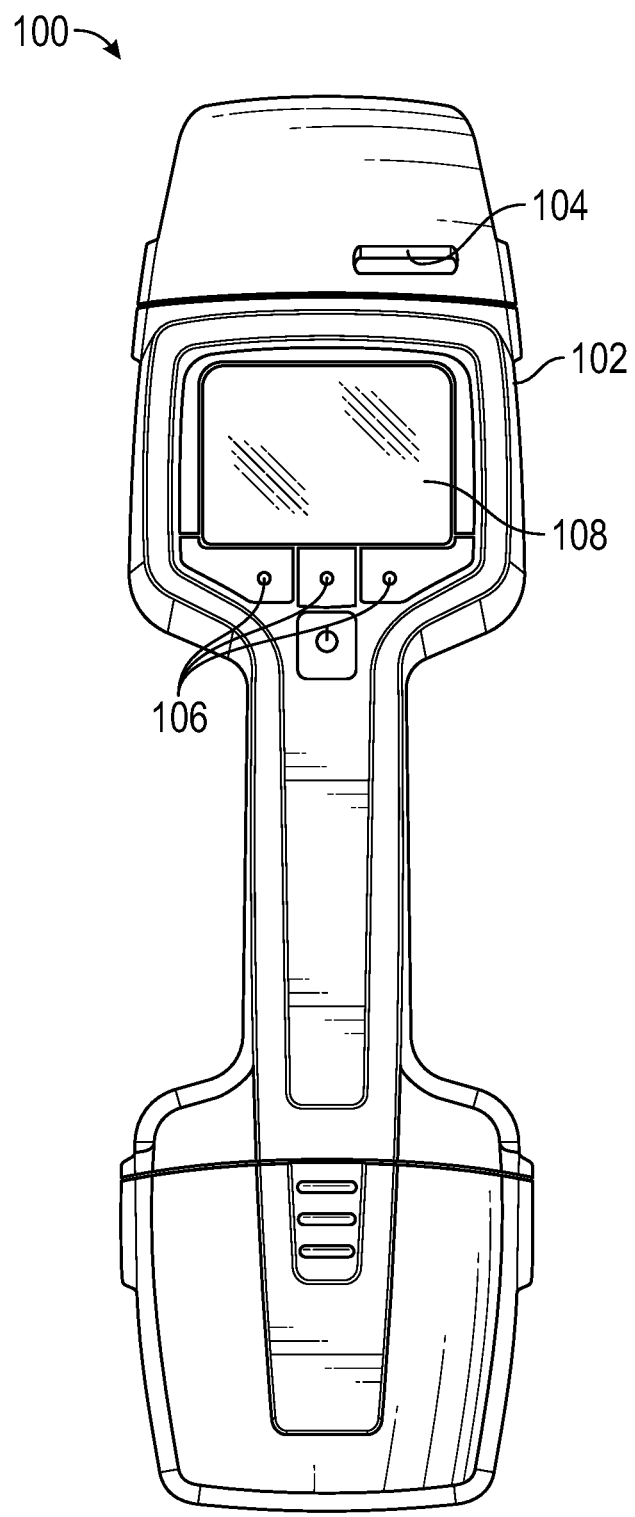
FIG. 1 illustrates an external view of a trace material detection device in accordance with an embodiment of the disclosure.

Embodiments of the present disclosure and their advantages are best understood by referring to the detailed description that follows. It should be appreciated that like

DETAILED DESCRIPTION

In accordance with various embodiments disclosed herein, a non-volatile acid is combined with 2-[5-methoxy-2-(4-phenyl-quinoline-2yl)-phenyl]-ethanol (PQP) to form protonated PQP. The chemical structure of PQP is provided below.

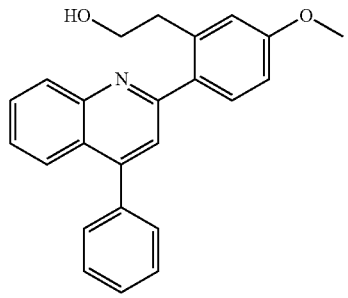 [SMILES: COc1ccc(-c2cc(-c3ccccc3)c3ccccc3n2)c(CCO)c1]

2-[5-methoxy-2-(4-phenyl-quinoline-2yl)-phenyl]-ethanol (PQP)

The non-volatile acid protonates the nitrogen of the quinolone part of the molecule, making the molecule fluorescent. The protonated PQP enhances the detection of one or more materials of interest. A chemical reporter that includes the protonated PQP then receives an amine-based substance and responds to the amine-based substance to produce a detectable result.

Devices and related methods are provided in accordance with a variety of techniques to detect the presence of trace chemicals corresponding to materials of interest using protonated PQP. In this regard, the protonated PQP exhibits a change in fluorescence when exposed to certain amine-based substances.

Various amine-based substances, including methamphetamine and cocaine, react with the protonated PQP to remove the hydrogen from the nitrogen of the quinolone part of the molecule. This reaction deprotonates the protonated PQP to cause a change in fluorescence.

The protonated PQP responds to the amine-based substance to provide a detectable response. This response may be the result of a change in the protonated PQP that may be detected at a particular type of detector of the chemical reporter, which signals the presence of a material of interest (e.g., an amine-based substance). In exemplary embodiments, the change is a change in fluorescence of the protonated PQP that is detected by an optical detector. Thus, materials of interest are identified in a convenient, low cost, rapid, and highly portable manner.

Advantageously, the chemical reporter is operable to detect a variety of amine-based substances that can deprotonate (or remove the proton from) the protonated PQP. Thus, rather than being specific to a single substance, the chemical reporter is able to detect a wide variety of amine-based substances, including, but not limited to, methamphetamine, methamphetamine hydrochloride, cocaine, cocaine hydrochloride, 3,4-methylenedioxymethamphetamine (MDMA), MDMA hydrochloride, heroin, and heroin hydrochloride.

In some embodiments, the above-described detection techniques may be combined with additional chemical detection techniques to provide methods and systems for detecting additional classes of materials. For example, certain peroxide-based explosives, such as triacetone triperoxide (TATP), hydrogen peroxide, and urea hydrogen peroxide may be detected using, for example, luminescent methods. In another example, certain explosive-related compounds, such as 2,4,6-trinitrotoluene (TNT), may be detected using fluorescent methods.

Turning now to the drawings, FIG. 1 illustrates an external view of a trace material detection device 100 in accordance with an embodiment of the disclosure. For example, in some embodiments, device 100 may be implemented as a handheld portable detector capable of detecting explosives, narcotics, and/or other materials.

As shown, device 100 includes a housing 102, a slot 104, user controls 106, and a display 108. In various embodiments, additional components of device 100 (e.g., further illustrated in FIG. 2) may be distributed at physical locations internal to and/or external to housing 102.

In operation, sampling media may be brought into physical contact with one or more surfaces to be tested. For example, in some embodiments, a user may wipe the media (e.g., also referred to as a "sampling swab") against a surface of interest to collect trace amounts of one or more test substances resident on the surface. The user then inserts the media into slot 104 after which additional operations and analysis are performed as further discussed herein. In some embodiments, the media may be implemented using an appropriate substrate such as polytetrafluoroethylene (PTFE), an aramid polymer, polyethylene, polyester, paper, and/or other materials.

In some embodiments, use of the media may not be necessary, as an inlet may be used to directly sample ambient air for vapor-phase analytes. Additional devices may be used to direct the analytes into the inlet, such as an air filter/concentrator positioned in the flow path of the analytes.

User controls 106 receive user input to operate device 100. As shown in FIG. 1, user controls 106 may be implemented as physical buttons. In other embodiments, user controls 106 may be implemented by one or more keyboards, levers, joysticks, touchscreens, and/or other controls. In some embodiments, user controls 150 may be integrated with display 108 as a touchscreen.

Display 108 presents information to the user of device 100. For example, FIG. 1 illustrates a warning message provided on display 108 in response to a detected material. In various embodiments, display may be implemented as a liquid crystal display (LCD), an organic light emitting diode (OLED) display, and/or any other appropriate display.

Figure 2:
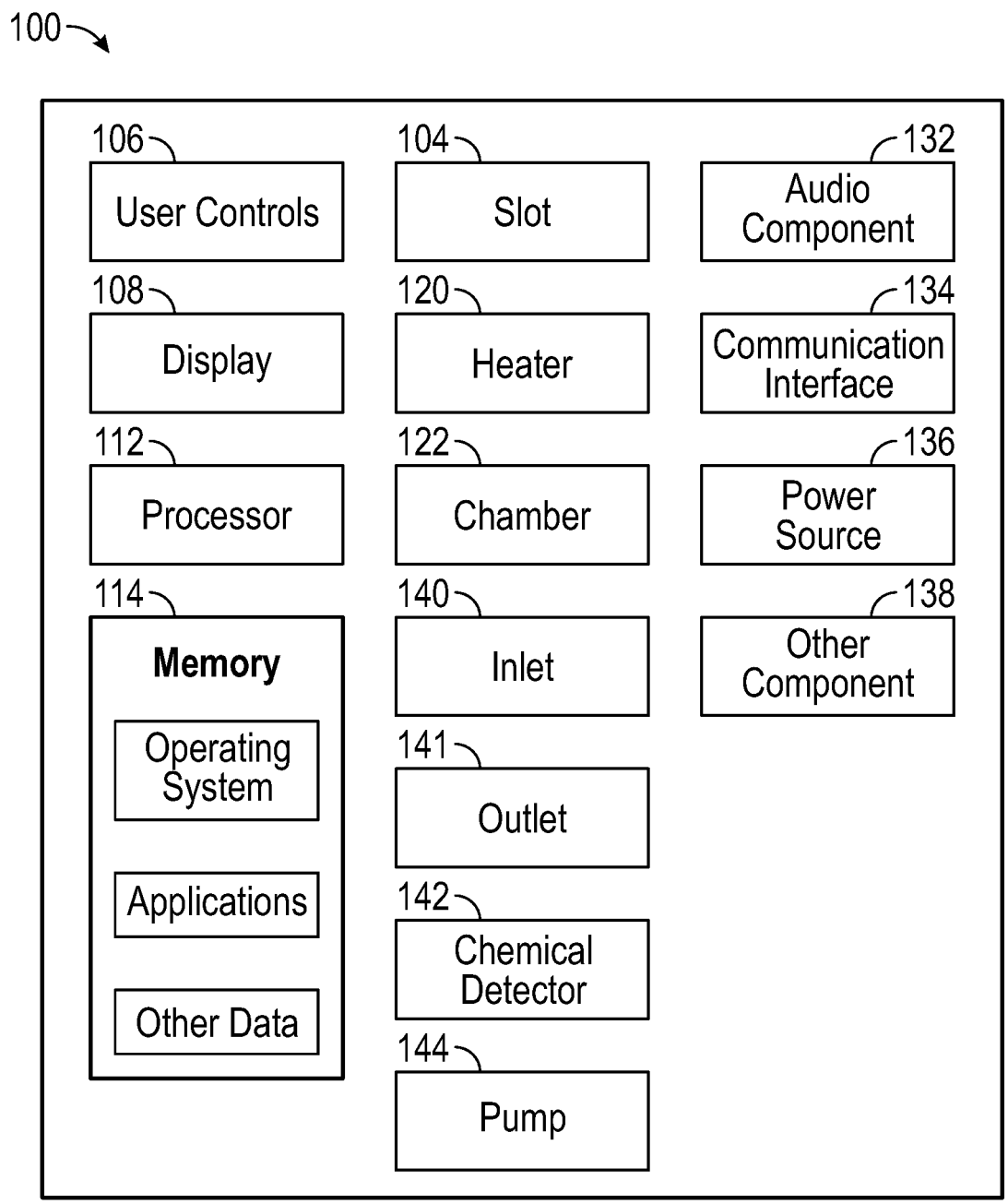
FIG. 2 illustrates a block diagram of a trace material detection device in accordance with an embodiment of the disclosure.

Additional features of device 100 are further illustrated in FIG. 2. FIG. 2 illustrates a block diagram of device 100 in accordance with an embodiment of the disclosure. In addition to several previously discussed components shown in FIG. 1, FIG. 2 further illustrates a processor 112, a memory 114, a heater 120, a chamber 122, an audio component 132, a communication interface 134, a power source 136, an inlet 140, an outlet 141, a chemical detector 142, a pump 144, and other components 138.

Processor 112 may be implemented as one or more microprocessors, microcontrollers, system on a chip (SoC), application specific integrated circuits (ASICs), programmable logic devices (PLDs) (e.g., field programmable gate arrays (FPGAs), complex programmable logic devices (CPLDs), field programmable systems on a chip (FPSCs), or other types of programmable devices), or other processing devices used to control the operations of device 100. In this regard, processor 112 may execute machine readable instructions (e.g., software, firmware, or other instructions) stored in memory 114.

Memory 114 may be implemented as a machine readable medium storing various machine readable instructions and data. For example, in some embodiments, memory 114 may store an operating system 115 and one or more applications 116 as machine readable instructions that may be read and executed by processor 112 to perform various operations described herein. Memory 114 may also store various types of data 117 including, for example, chemical profiles, test sample identification results, and/or other information used or provided by the various components of device 100. In various embodiments, memory 114 may be implemented to store such instructions and data in a non-transitory manner and/or may be implemented with both transitory and non-transitory portions to selectively store all or portions of such instructions and data in either manner as appropriate.

Heater 120 may be implemented as one or more heaters (e.g., heaters 120A, 120B, and 120C further discussed herein) used to heat test samples (e.g., provided on a sampling swab) to a desired temperature such that the test samples at least partially vaporize to provide analytes for chemical detection. In certain embodiments, heater 120 may be implemented as one or more heaters (720A, 720B, and 720C further discussed herein) used to heat a gas sample to facilitate the movement of analytes in the gas sample from an external environment to a chemical detector. In some embodiments, heater 120 may be a resistive heater configured to heat the test samples, however other configurations may be used in other embodiments.

Chamber 122 provides a recessed volume within housing 102 and receives the media inserted through slot 104. While disposed in chamber 122, the media may be heated by heater 120.

Audio component 132 may be implemented, for example, as a speaker or other transducer with corresponding driver circuitry to provide audible sounds to a user of device 100. For example, in some embodiments, audio component 132 may provide audible signals in response to manipulation of user controls 106 and/or in response to the operations of processor 112 (e.g., to indicate that a particular material is present or is not present).

Communication interface 134 may be implemented as a wired and/or wireless interface connect device 100 (e.g., by Universal Serial Bus (USB), Ethernet, WiFi, Bluetooth, cellular, infrared, radio, and/or other protocols) with various external devices to update operating system 115, update applications 116, and/or communicate data 117. In some embodiments, communication interface 134 may connect to external power sources (e.g., a power outlet) to charge a battery of power source 136 and/or to directly power device 100.

Power source 136 may be implemented, for example, as a battery to permit mobile and remote use of device 100, a solar power source, a fuel cell, or wall power. In some embodiments, power source 136 may be a removable battery. Other components 138 may also be provided as appropriate for various types of devices 100 to support, for example, application specific operations of such devices.

Inlet 140, chemical detector 142, and pump 144 (e.g., implemented as an emission-based detector and/or using other technologies) may be used with heater 120 to provide a swab-based thermal desorber to perform vapor-based material detection as further discussed herein. In some embodiments, inlet 140 can directly sample ambient air for vapor-phase analytes without the need for the swab-based thermal desorber. For example, air from the ambient environment may be directly drawn into inlet 140, through chemical detector 142, and out of outlet 141 using pump 144.

Figure 3:
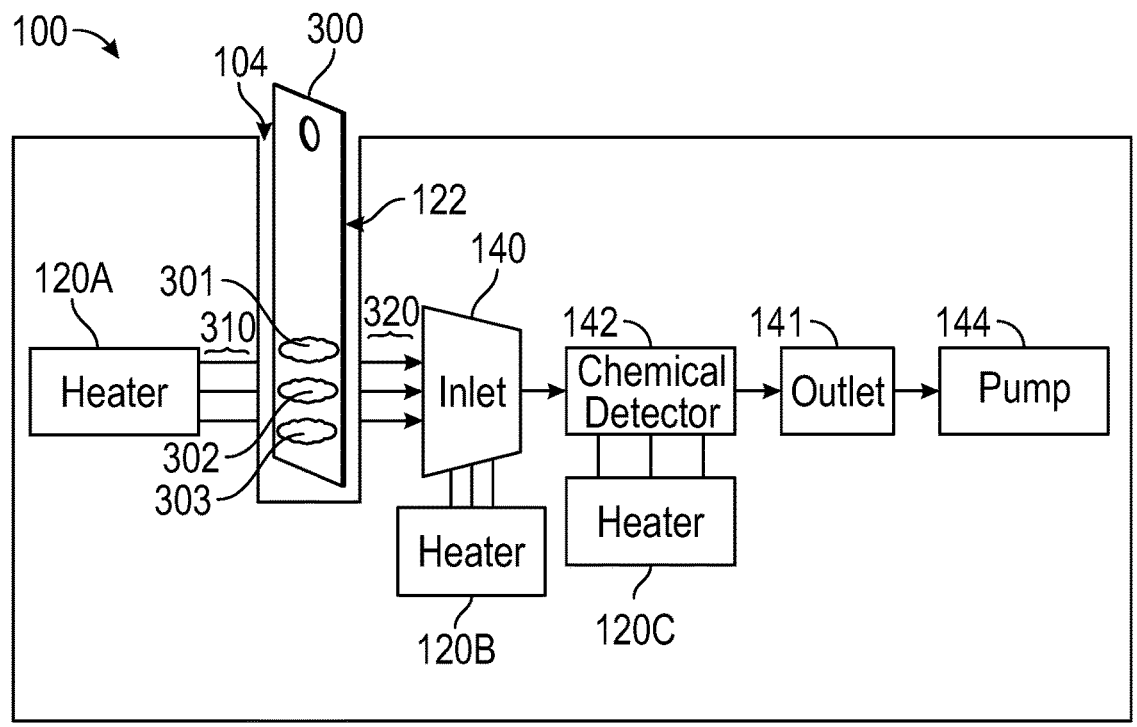
FIG. 3 illustrates an operational flow of analytes through a trace material detection device in accordance with an embodiment of the disclosure.

FIG. 3 illustrates an operational flow of analytes through device 100 in accordance with an embodiment of the disclosure. As shown, media 300 has been inserted through slot 104 in housing 102 and is positioned in chamber 122. Media 300 includes test samples 301, 302, and 303 which correspond to three different materials under test that have been picked up by the user's application of media 300 against one or more surfaces of interest.

As shown, heater 120 is implemented in multiple portions 120A, 120B, and 120C. Heater 120 operates (e.g., in response to control signals provided by processor 112) to apply heat 310 to media 300 and samples 301, 302, and 303 to raise their temperatures to a desired desorption temperature. In some embodiments, the detection temperature may be in the range of approximately 90 degrees C. to approximately 160 degrees C., however higher or lower temperatures may be used as desired.

In some embodiments, heaters 120A and 120B may be implemented to contact media 300. For example, heaters 120A and 120B may be mechanically moved to place the heaters 120A and 120B in contact with or in close proximity to media 300.

In FIG. 3, test sample 301 is TNT, test sample 302 is methamphetamine hydrochloride, and test sample 303 is TATP, all of which may be detected by appropriate portions of chemical detector 142.

In this regard, test samples 301, 302, and 303 may be materials that partially or completely vaporize in response to heat 310 applied by heater 120 to provide analytes 320 (e.g., corresponding to vaporized portions of test samples 301, 302, and 303). The vaporized materials may exhibit various vapor pressures that facilitate the ability of pump 144 and chemical detector 142 to appropriately receive the analytes 320 (e.g., RDX has a vapor pressure of $5 \times 10^{-7}$ Torr at 20 degrees C., TNT has a vapor pressure of $2 \times 10^{-5}$ Torr at 20 degrees C., glycerol has a vapor pressure of $2.5 \times 10^{-3}$ Torr at 50 degrees C., and ethanol has a vapor pressure of 45 Torr at 20 degrees C.). Pump 144 operates to draw analytes 320 in and through inlet 140 into chemical detector 142 and out through outlet 141. Based on interactions between analytes 320 and chemical detector 142 (e.g., performing trace detection), the presence of certain materials of interest may be determined.

Figure 4:
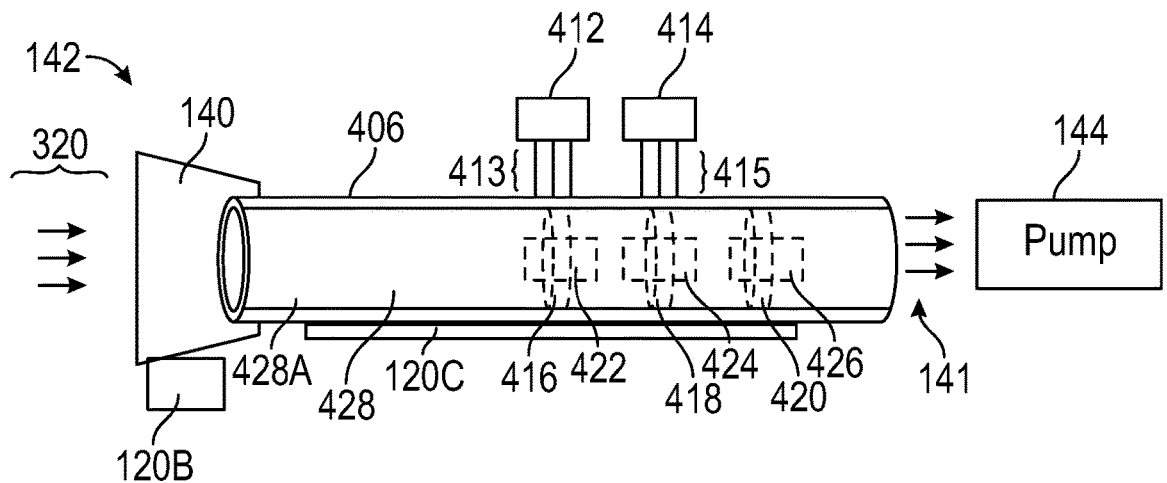
FIG. 4 illustrates a partial cross section view of a chemical detector with chemical reporters disposed along a sensing channel in accordance with an embodiment of the disclosure.
Figure 5:
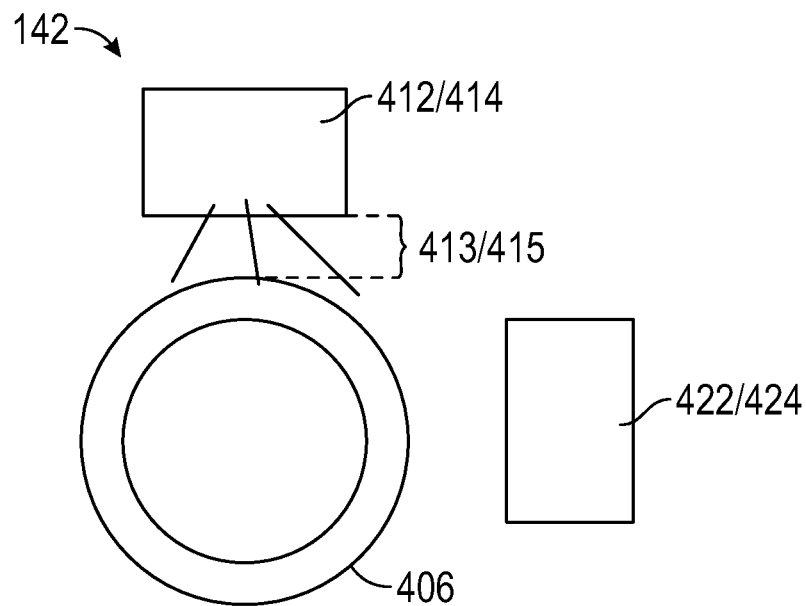
FIG. 5 illustrates a front view of a chemical detector with chemical reporters disposed along a sensing channel in accordance with an embodiment of the disclosure.

FIGS. 4 and 5 illustrate various views of chemical detector 142 of device 100 in accordance with embodiments of the disclosure. As shown, the detector 142 includes an inlet 140, an outlet 141, a tip heater 120B, a substrate reporter surface 406 (e.g., implemented as a capillary tube providing a flow path in these particular illustrated embodiments), a sensing channel 428 (e.g., implemented as a cavity within a capillary tube in these particular illustrated embodiments), a reporter heater 120C, various chemical reporters 416, 418, and 420, illumination sources 412 and 414 (e.g., also referred to as excitation sources) associated with chemical reporters 416 and 418, and response detectors 422, 424, and 426 associated with chemical reporters 416, 418, and 420.

Illumination sources 412 and 414 are optional, in that they are not required in chemical detection techniques that do not involve illumination of chemical reporters 416 and 418. For example, when a chemical reporter responds to a material of interest by exhibiting a change in resistivity, illumination sources 412 and 414 are not needed. In this case, the response of the chemical reporter is exhibited by a corresponding change in current or voltage that is detected by an appropriate detector.

As shown, when implemented as a capillary tube, substrate reporter surface 406 defines sensing channel 428, which provides a flow path through which vapor-phase analytes 320 pass through and interact with chemical reporters 416, 418, and 420.

Analytes 320 pass through inlet 140, where analytes 320 may be heated by tip heater 120B. Tip heater 120B maintains inlet 140 at a temperature sufficient to keep analytes 320 in the vapor-phase. More specifically, tip heater 120B prevents loss of analytes 320 while traveling through inlet 140 toward chemical reporters 416, 418, and 420. Pump 144 continues to pull the air with analyte(s) 320 in through inlet 140 and provides the ability to move vapor-phase analytes 320 from inlet 140 to sensing channel 428 and chemical detectors 416, 418, and 420, and out through outlet 141. Reporter heater 120C heats the interior surface of substrate reporter surface 406 to reduce the formation of "cold spots" where analytes 320 can lump together. In addition, reporter heater 120C helps analytes 320 desorb from chemical reporters 416, 418, and 420 to improve subsequent detection of analytes. In some embodiments, sensing channel 428 includes an initial portion 428A to prevent overheating of chemical reporters 416, 418, and 420 due to their proximity to tip heater 120B.

Analytes 320 move over each of the chemical reporters 416, 418, and 420. In some embodiments, chemical reporters 416, 418, and 420 may be placed in any order. In addition, although illustrated as discrete sections in FIG. 4, chemical reporters 416, 418, and 420 may contact each other and/or may be layered over each other in some embodiments.

In this example, chemical reporter 416 is operable to detect certain military explosives (or explosive-related compounds) and may be termed a "military explosives chemical reporter." In some embodiments, military explosives chemical reporter 416 includes an amplifying fluorescent polymer or other military chemical reporter. The intensity of light emitted by the amplifying fluorescent polymer varies in response to interaction of the amplifying fluorescent polymer with analytes 320.

For example, the binding of one analyte molecule to the amplifying fluorescent polymer quenches the emission of many polymer repeat units. Thus, when an analyte of interest lands on a polymer binding site, many polymer repeat units in the vicinity of the bound analyte do not emit absorbed light as fluorescence. As a result, the polymer fluorescence is said to be "quenched" by the adsorption of the analyte molecule.

In various embodiments, military explosives chemical reporter 416 is associated with illumination source 412 having an associated wavelength and response detector 422 (e.g., an optical detector). Illumination source 412 (e.g., a LED) emits light 413 in a wavelength that interacts with the amplifying fluorescent polymer to cause the amplifying fluorescent polymer to generate an emission. In certain embodiments, the wavelength is about 400 nm (e.g., 365 nm). In some embodiments, illumination source 412 only illuminates the portion of military explosives chemical reporter 416 that contains the amplifying fluorescent polymer. Response detector 422 (e.g., a photodiode) is positioned to receive the emission generated by the amplifying fluorescent polymer to detect the presence of one or more analytes 320. As shown in FIG. 5, in some embodiments, illumination source 412 and response detector 422 are positioned to be out of line of sight, for example 90 degrees apart. This ensures that light emitted by illumination source 412 is not captured by response detector 422, so that response detector 422 captures mostly the emission generated by the amplifying fluorescent polymer. Other dispositions of illumination source 412 and response detector 422 are contemplated, and illumination source 412 and response detector 422 can be positioned in any desired configuration (e.g., in close proximity or co-located in some embodiments). Inlet 140 is not shown in FIG. 5 for purposes of clarity.

Examples of analytes that are detectable by military explosives chemical reporter 416 include TNT (e.g., test sample 301). Other substances that may be detected are disclosed in U.S. Pat. No. 6,558,626, which is incorporated by reference in its entirety by express reference thereto.

In an example, chemical reporter 418 is operable to detect certain amine-based substances, such as amine compounds like methamphetamine hydrochloride (e.g., test sample 302), and may be termed an "amine chemical reporter." The amine chemical reporter 418 includes protonated PQP, which is fluorescent. Changes in the fluorescence (i.e., increases or decreases in the response of the protonated PQP of the amine chemical reporter 418 to light) establish the presence of an amine compound. For example, upon reaction of an amine compound with the protonated PQP of the amine chemical reporter 418, the protonated PQP may undergo a change in fluorescent response intensity. In some embodiments, the amine compound deprotonates the protonated PQP of the amine chemical reporter 418 to produce a decreased fluorescent response.

In various embodiments, to prepare the protonated PQP, PQP is combined with a non-volatile acid and a polymer (e.g., polystyrene). The non-volatile acid does not exhibit a substantial vapor pressure and includes, but is not limited to, a carboxylic acid, a carboxylic acid containing polymer, and/or a sulfonic acid containing polymer. Examples of suitable carboxylic acids include hexacosanoic acid and stearic acid. Suitable carboxylic acid containing polymers include polyacrylic acid and polymethacrylic acid. A suitable sulfonic acid containing polymer includes polystyrenesulfonic acid.

In exemplary embodiments, PQP at a concentration of 2.5 mg/mL, polystyrene at a concentration of 5 mg/mL, and hexacosanoic acid at a concentration of 2.5 mg/mL are combined and mixed together. The mixture is then spin-coated on a surface (e.g., a capillary tube or a flat substrate) and allowed to dry (e.g., in air or in an oven).

Amine chemical reporter 418 is associated with illumination source 414 having an associated wavelength (e.g., 365 nm or 405 nm) and response detector 424 (e.g., an optical detector).

Illumination source 414 (e.g., a LED) emits light 415 in a wavelength that interacts with the protonated PQP of the amine chemical reporter 418 to cause the protonated PQP to generate an emission. Response detector 424 is positioned to receive the emission generated by the protonated PQP of the amine chemical reporter 418 to detect the presence of an amine compound. Response detector 424 detects the changes in response of the protonated PQP of the amine chemical reporter 418 to thereby establish the presence of an amine compound. Illumination source 414 and response detector 424 may be positioned out of line of sight as shown in FIG. 5.

In some embodiments, an initial response baseline may be first established for the protonated PQP of the amine chemical reporter 418. To establish the baseline response for the protonated PQP of the amine chemical reporter 418, a user activates illumination source 414 and heaters 120A, 120B, and 120C, allowing each to achieve operational conditions. Then the user presents substrate reporter surface 406 (implemented as a capillary tube in the illustrated embodiments), free of analytes 320, to illumination source 414 and response detector 424 to produce a detectable response from the protonated PQP of the amine chemical reporter 418. Thus, any response resulting from this process is free of influence from an amine compound, and can be used to detect whether a change in response occurs.

In an example, chemical reporter 420 is operable to detect certain peroxide-based explosives, such as peroxide-containing compounds like hydrogen peroxide and urea hydrogen peroxide, and peroxide precursors like TATP (e.g., test sample 303), and may be termed a "peroxide chemical reporter." In some embodiments, peroxide chemical reporter 420 includes a light-emitting peroxide-reactive compound and is associated with response detector 426 (e.g., an optical detector). Light-emitting materials suitable for use may be any luminescent material, including dyes, oligomers, polymers, and combinations thereof. The light-emitting material may be selected to exhibit certain properties, such as a particular emission wavelength, high quantum yield, high output light efficiency when formulated in a peroxide reactive system, and/or compatibility (e.g., solubility) with one or more components of the system. Additional details regarding the light-emitting materials are found in U.S. Pat. No. 9,005,524, which is incorporated by reference in its entirety by express reference thereto.

The light-emitting peroxide-reactive material responds to the hydrogen peroxide generated from peroxide-containing compounds or peroxide precursors to produce energy in the form of the emission of a photon. In some embodiments, the resulting energy can stimulate luminescence of the light-emitting peroxide-reactive material such that light energy is emitted. The resulting emission may be detected by response detector 426, which signals the presence of hydrogen peroxide (and a peroxide precursor and/or a peroxide-containing compound).

In certain embodiments, two of the three chemical reporters 416, 418, and 420 may include the same material to detect similar types of compounds. For example, chemical reporters 416 and 418 (or chemical reporters 416 and 420) may each include protonated PQP to detect the presence of amine compounds. In this way, an amine compound can interact with and be detected at more than one chemical reporter.

Figure 7:
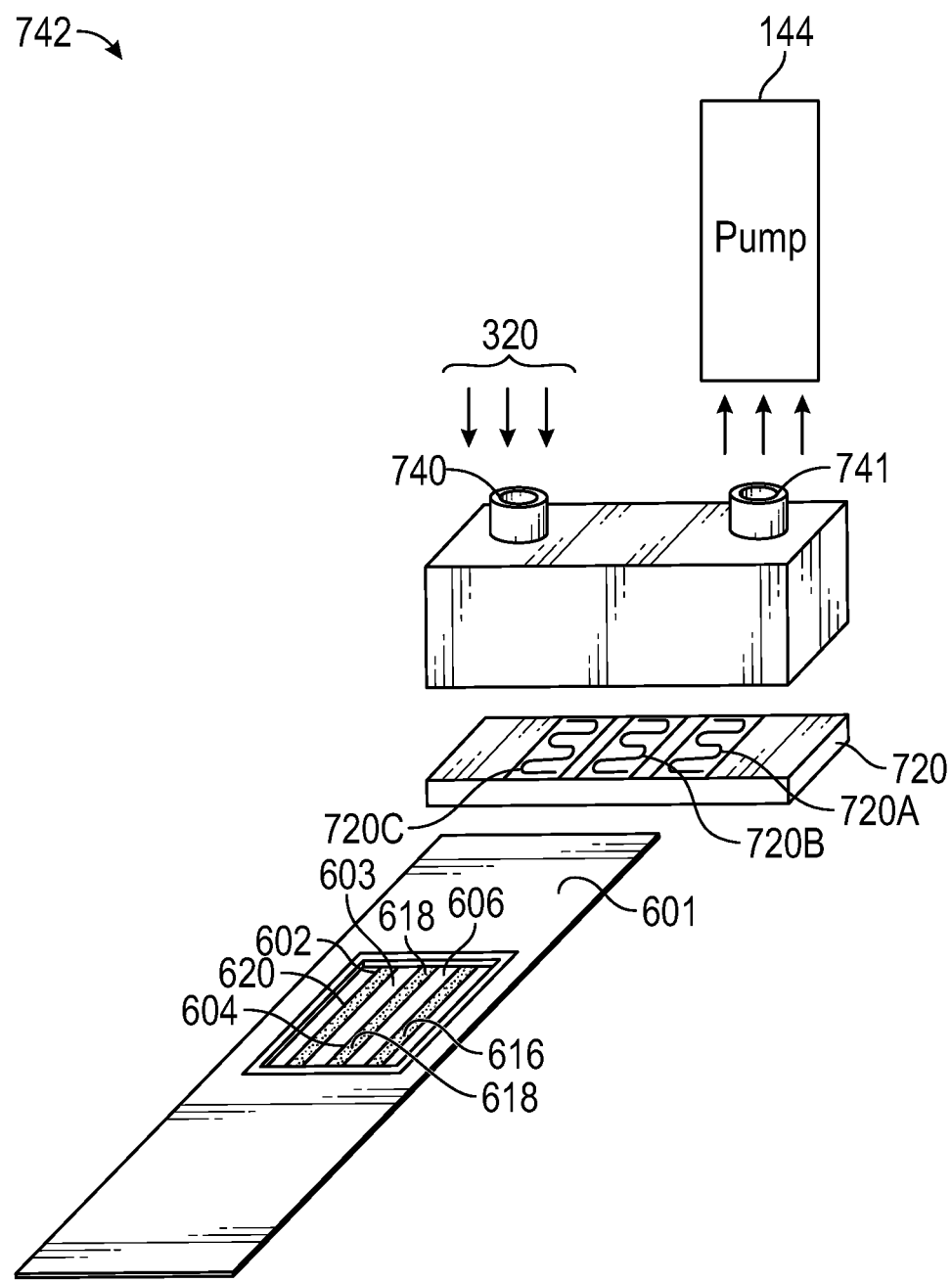
FIG. 7 illustrates a perspective view of a chemical detector with chemical reporters disposed along a flat surface in accordance with an embodiment of the disclosure.
Figure 8:
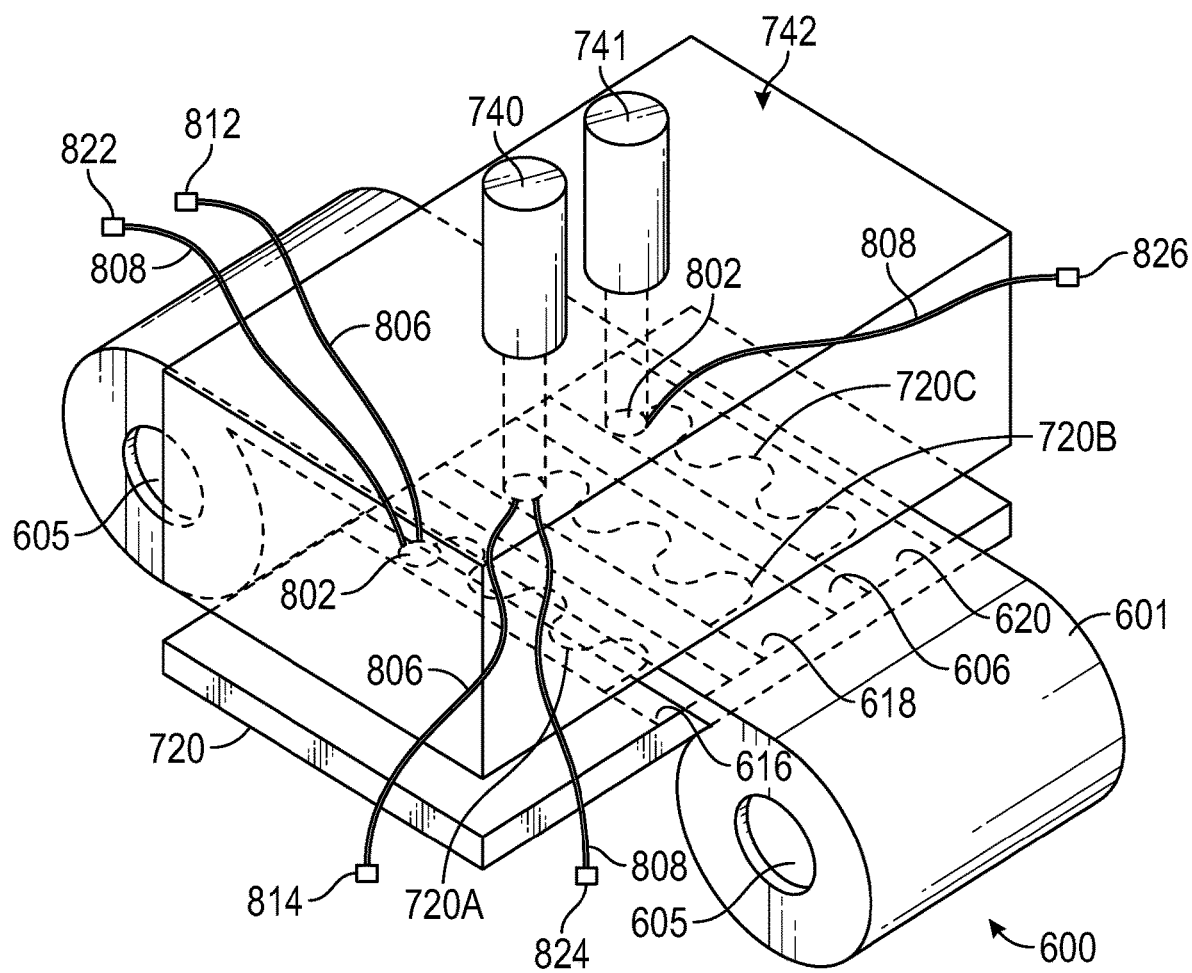
FIG. 8 illustrates a perspective view of a chemical detector with chemical reporters disposed along a flat surface in combination with a cartridge and a detection system in accordance with an embodiment of the disclosure.

Other chemical detector embodiments are also contemplated. For example, FIGS. 6-8 illustrate various components of a chemical detector 742 that may be used in addition to or in lieu of chemical detector 142.

Figure 6:
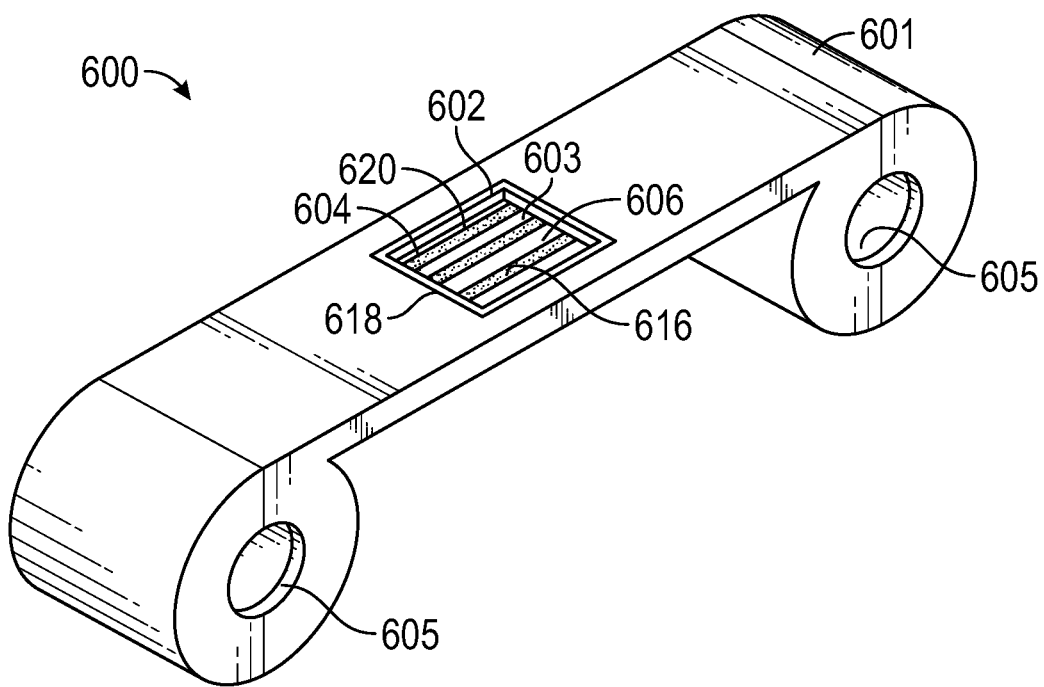
FIG. 6 illustrates a perspective view of a cartridge containing a flat substrate reporter surface in accordance with an embodiment of the disclosure.

FIG. 6 illustrates a cartridge 600 with an upper surface 601 containing a flat substrate reporter surface 606. Cartridge 600 exposes a portion of substrate reporter surface 606 through window 603 to a gas sample. As shown, substrate reporter surface 606 includes chemical reporters 616, 618, and 620. Chemical reporters 616, 618, and 620 correspond to chemical reporters 416, 418, and 420. Accordingly, the discussion of chemical reporters 416, 418, and 420 herein is also applicable to chemical reporters 616, 618, and 620.

Sample area 604 exposes chemical reporters 616, 618, and 620 to a gas sample containing analytes 320. To prevent premature exposure of substrate reporter surface 606 to the environment, substrate reporter surface 606 may be sealed within cartridge 600 with seal 602 at window 603. Seal 602 may be made from a variety of materials such as felt, rubber, paper, silicone, neoprene, other non-responsive materials, and combinations thereof. Window 603 provides access for the gas sample to interact with chemical reporters 616, 618, and 620 carried by substrate reporter surface 606. Sample area 604 is positioned within window 603. Window 603 may be open both above and below substrate reporter surface 606.

In some embodiments, cartridge 600 automatically advances substrate reporter surface 606 through sample area 604 to optimize the exposure of chemical reporters 616, 618, and 620. For example, substrate reporter surface 606 may be advanced from the edge of an exposed area using reels 605 until an entirely new, unexposed area of substrate reporter surface 606 is within window 603. The advancing mechanism for cartridge 600 may be of any type known in the art such as electric or pneumatic motors. In various embodiments, when cartridge 600 reaches the end of the unexposed substrate reporter surface 606, a user is able to remove and insert a new cartridge 600. In certain embodiments, cartridge 600 may be implemented in a similar manner as one or more cartridges or modules described in U.S. Pat. No. 9,448,180, which is incorporated by reference in its entirety by express reference thereto.

FIG. 7 illustrates chemical detector 742 in accordance with an embodiment of the disclosure. Similar to chemical detector 142, chemical detector 742 includes an inlet 740, a pump 144, an outlet 741, a substrate reporter surface 606 (e.g., implemented as a flat substrate as described in FIG. 6), a reporter heater 720 (including heaters 720A, 720B, and 720C), and various chemical reporters 616, 618, and 620. Chemical reporters 616, 618, and 620 are shown on an upper surface 601 of a cartridge for clarity. As discussed further below, these components correspond to or are implemented in substantially the same manner as the components in chemical detector 142.

One difference between chemical detector 742 and chemical detector 142 is that chemical detector 142 uses a capillary tube as a substrate reporter surface while chemical detector 742 uses a flat surface as a substrate reporter surface. Additional differences lie in the placement of the various components forming the detectors 142 and 742 as further discussed below.

As shown in FIG. 7, ambient air containing vapor-phase analytes 320 is pulled in through inlet 740, over substrate reporter surface 606, and out through outlet 741 using pump 144. Heater 720 (implemented as 720A, 720B, and 720C) heats the interior surface of substrate reporter surface 606 (implemented here as a flat substrate) and the air containing the analytes 320. Heating, in some embodiments, keeps the analytes 320 in a gaseous state.

In various embodiments, substrate reporter surface 606 is positioned between inlet 740 and heater 720. Substrate reporter surface 606 carries chemical reporters 616, 618, and 620. As pump 144 operates to draw air in through inlet 740, analytes 320 move over each of the chemical reporters 616, 618, and 620. The interaction between analytes 320 and chemical reporters 616, 618, and 620 may produce a fluorescent response, a change in fluorescence, a luminescent response, or a change in luminescence.

FIG. 8 illustrates chemical detector 742 (including a detection system) in combination with cartridge 600. Detection system detects responses to an analyte(s) 320 exposed to the portion of the substrate reporter surface 606 carrying chemical reporters 616, 618, and 620. As shown in FIG. 8, ports 802 may be positioned below substrate reporter surface 606. Ports 802, however, may be positioned above, below, or anywhere in an optical line of sight. Detection system includes illumination sources 812 and 814 (e.g., LEDs) having an associated wavelength and response detectors 822, 824, and 826 (e.g., optical detectors). Response detector 822 is associated with illumination source 812, and response detector 824 is associated with illumination source 824. Illumination sources 812 and 814, and response detectors 822, 824, and 826 are positioned to be in direct or indirect optical communication with ports 802. As shown, ports 802 have fiber optic cables 806 and 808 providing the communication between optical ports 802 and illumination sources 812 and 814 and response detectors 822, 824, and 826.

Illumination source 812 illuminates chemical reporter 616. For example, light at a certain wavelength propagates through fiber optic cable 806 and optical port 802 to illuminate chemical reporter 616. Upon response of chemical reporter 616 to an analyte(s) 320, response detector 822 detects the response. For example, fiber optic cable 808 communicates a detected change in fluorescence from chemical reporter 616 to response detector 822. Similarly, illumination source 814 illuminates chemical reporter 618. Upon response of chemical reporter 618 to an analyte(s) 320, response detector 824 detects the response. For example, fiber optic cable 808 communicates a detected change in fluorescence from chemical reporter 618 to response detector 824. Lastly, response detector 826 detects a response (e.g., luminescent response) of chemical reporter 620 to an analyte(s) 320.

Figure 9:
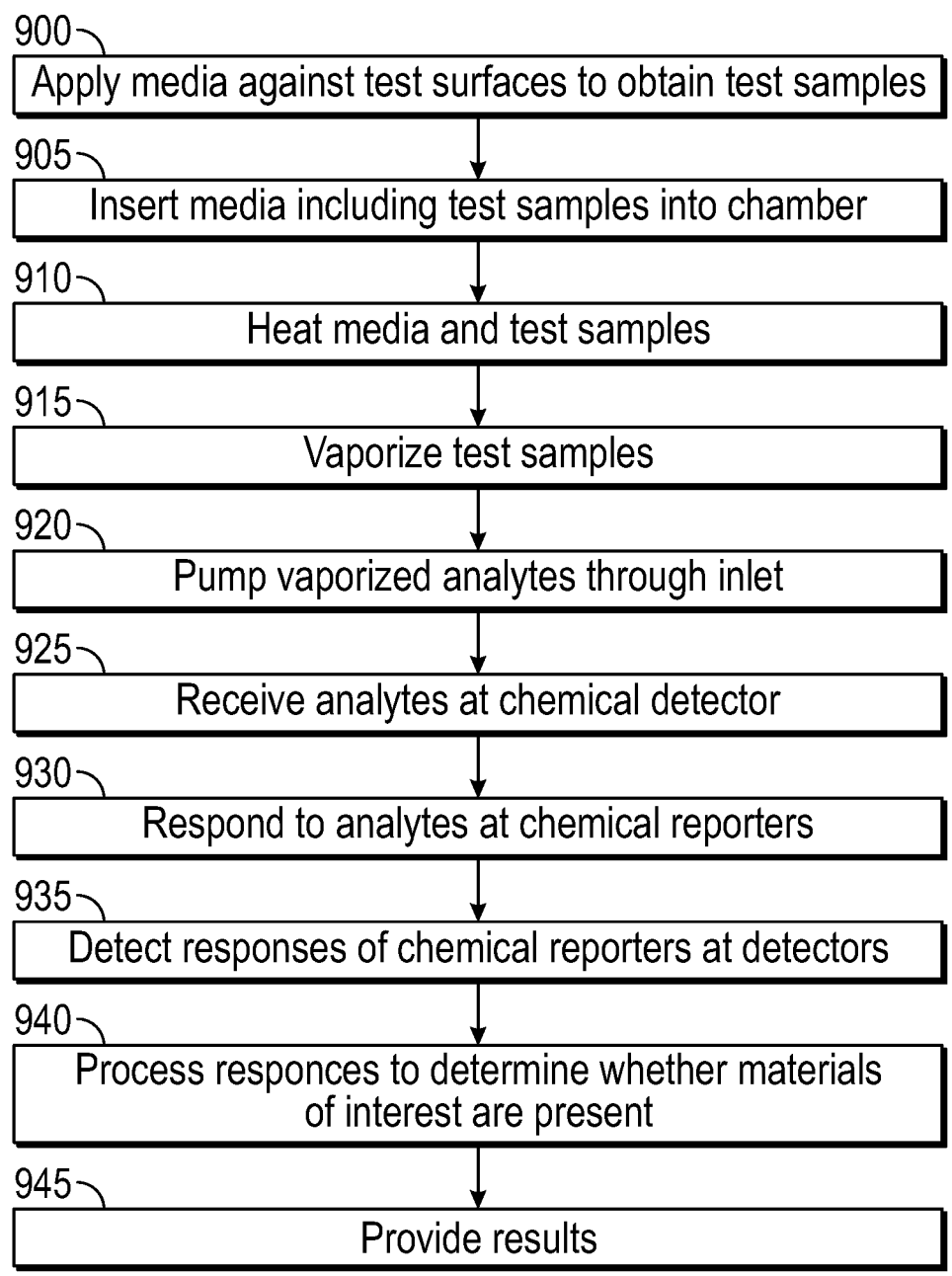
FIG. 9 illustrates a process of operating a trace material detection device in accordance with an embodiment of the disclosure.

FIG. 9 illustrates a process of operating device 100 in accordance with an embodiment of the disclosure. The process of FIG. 9 may be used with chemical detector 142 and/or chemical detector 742.

In block 900, a user applies media 300 against a test surface (e.g., a package, luggage, clothing, or other article) to obtain one or more test samples (e.g., test samples 301, 302, and 303 as shown in FIG. 3) corresponding to trace materials residing on the test surfaces.

In block 905, the user inserts media 300 through slot 104 and into chamber 122 as shown in FIG. 3. In block 910, heater 120 applies heat 310 to media 300 and test samples 301, 302, and 303. In various embodiments, processor 112 may operate heater 120 in response to the user's operation of one or more user controls 106 and/or automatically in response to the insertion of media 300 into chamber 122.

In block 915, test samples 301, 302, and 303 are at least partially vaporized to provide analytes 320 in response to heat 310 applied by heater 120. In various embodiments, heat is applied to both sides of media 300, as shown in FIG. 3.

In some embodiments, media 300 and chamber 122 are not required, such as when vapor-phase analytes 320 are directly drawn into inlet 140 from the ambient environment. Similarly, in embodiments using chemical detector 742, vapor-phase analytes 320 in the air are pulled in through inlet 740, without the need for media 300. In such embodiments, blocks 905, 910, and 915 may be omitted and the process of FIG. 9 may begin with block 920.

In block 920, pump 144 operates to draw analytes 320 through inlet 140/640 and out outlet 141/641. In block 925, analytes 320 are received by chemical detector 142/742 as shown in FIGS. 3 and 7.

In block 930, chemical reporters respond to the presence of analytes 320. For example, military explosives chemical reporter 416/616 may respond to the portion of analytes 320 corresponding to test sample 301, amine chemical reporter 418/618 may respond to the portion of analytes 320 corresponding to test sample 302, and peroxide chemical reporter 420/620 may respond to the portion of analytes 320 corresponding to test sample 303.

In block 935, responses of the chemical reporters to the analytes 320 are detected. For example, response detector 422/822 detects the response of military explosives chemical reporter 416/616 to the portion of analytes 320 corresponding to test sample 301, response detector 424/824 detects the response of amine chemical reporter 418/618 to the portion of analytes 320 corresponding to test sample 302, and response detector 426/826 detects the response of peroxide chemical reporter 420/620 to the portion of analytes 320 corresponding to test sample 303.

In block 940, processor 112 determines whether materials of interest are present based on the responses detected by response detectors 422/822, 424/824, and 426/826. In block 945, the results of block 940 are provided to the user, for example, by messages and/or graphics provided by display 108, audible notifications provided by audio component 132, and/or other techniques as appropriate.

Figure 10:
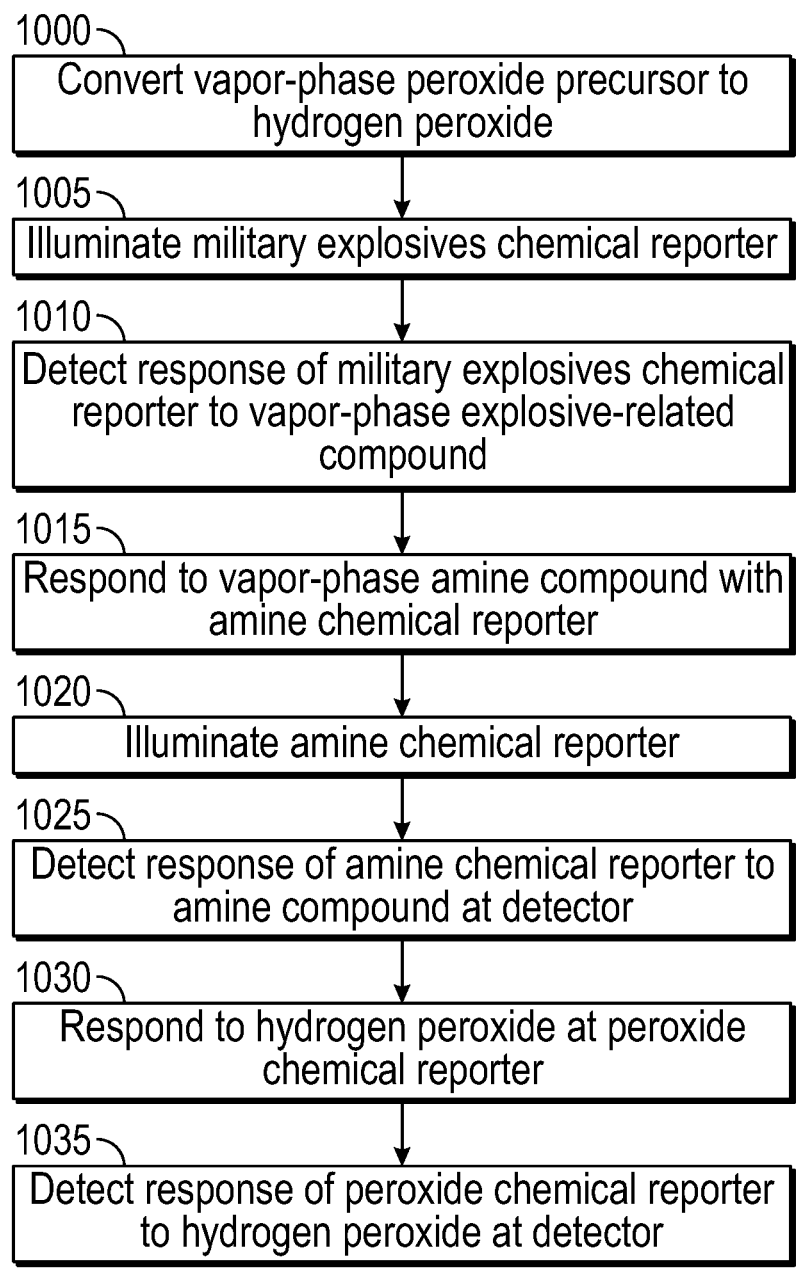
FIG. 10 illustrates a more detailed process of operating a trace material detection device in accordance with an embodiment of the disclosure.

FIG. 10 illustrates more process details performed during one or more of blocks 925-935 of FIG. 9 in embodiments that use emission (e.g., fluorescent and luminescent) techniques. In block 1000, a vapor-phase peroxide precursor (e.g., corresponding to test sample 303) is converted to hydrogen peroxide. Alternatively or additionally, a vapor-phase peroxide-containing compound may be broken down into hydrogen peroxide. In block 1005, a military explosives chemical reporter 416/616 is illuminated. In FIG. 4, military explosives chemical reporter 416 is illuminated by illumination source 412. Similarly, in FIG. 8, chemical reporter 616 is illuminated by illumination source 812. In block 1010, a response of the military explosives chemical reporter 416/616 to the portion of analytes 320 including an explosive-related compound is detected at response detector 422/822. For example, military explosives chemical reporter 416/616 may respond to an explosive-related compound to create a change in fluorescent response that is detected by response detector 422/822. In various embodiments, military explosives chemical reporter 416/616 may respond to the explosive-related compound by quenching the military explosives chemical reporter 416/616.

In block 1015, amine chemical reporter 418/618 responds to the vapor-phase amine compound. For example, the amine compound can deprotonate the protonated PQP of the amine chemical reporter 418/618. In block 1020, the amine chemical reporter 418/618 is illuminated. As shown in FIG. 4, illumination source 414 illuminates amine chemical reporter 418, and in FIG. 8, illumination source 814 illuminates chemical reporter 618.

In block 1025, a response of the amine chemical reporter 418/618 to the amine compound is detected by response detector 424/824. For example, the interaction between amine compound and the amine chemical reporter 418/618 may result in a change in the amine chemical reporter 418/618 that is detected by response detector 424/824. In various embodiments, processor 112 determines whether a particular material of interest (e.g., amine compound) is present in the test sample based on the response of the amine chemical reporter 418/618.

In block 1030, peroxide chemical reporter 420/620 responds to the hydrogen peroxide produced from the peroxide precursor (or the hydrogen peroxide from a peroxide-containing compound). In block 1035, a response of the peroxide chemical reporter 420/620 to the hydrogen peroxide is detected by response detector 426/826. For example, the interaction between the hydrogen peroxide and peroxide chemical reporter 420/620 may result in a luminescent response of the peroxide chemical reporter 420/620 that is detected by response detector 426/826.

Figure 11:
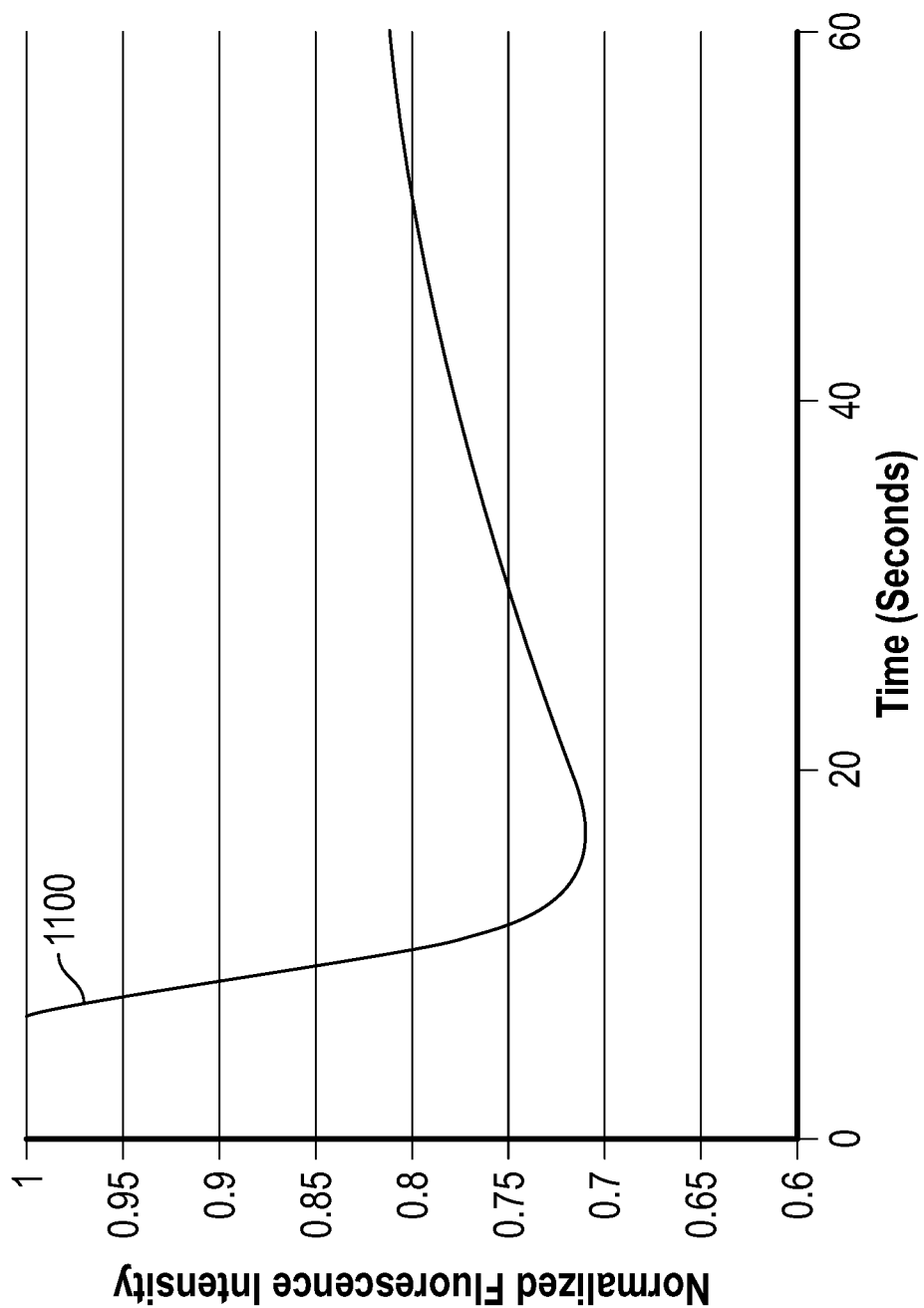
FIG. 11 illustrates a graph demonstrating a response of a chemical reporter to an amine compound in accordance with an embodiment of the disclosure.

FIG. 11 illustrates a graph 1100 demonstrating a response of an amine chemical reporter 418/618 to methamphetamine hydrochloride. The graph 1100 shows a decrease in fluorescence intensity as time progresses due to the deprotonation by the amine compound of protonated PQP in the amine chemical reporter 418/618.

In view of the present disclosure, it will be appreciated that devices and related methods are provided to detect the presence of trace chemicals corresponding to materials of interest using protonated PQP. The protonated PQP is responsive not only to amine compounds in the free-base form, but also to their hydrochloride salts, which have substantially lower vapor pressures. In addition, use of the protonated PQP facilitates relatively quick responses and recovery times.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as program code and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the present invention. Accordingly, the scope of the invention is defined only by the following claims.

What is claimed is:

1. A method comprising:
providing a chemical reporter of a chemical detector, the chemical reporter comprising protonated 2-[5-methoxy-2-(4-phenyl-quinoline-2y1)-phenyl]-ethanol (PQP);
receiving a vapor-phase amine compound at the chemical reporter; and
detecting, by the chemical detector, a response of the chemical reporter to the amine compound to determine whether the amine compound is present, wherein the detecting is a direct detecting of the amine compound by the protonated PQP.

2. The method of claim 1, further comprising:
illuminating the chemical reporter with an excitation source having an associated wavelength to provide the response as a change in fluorescence in the chemical reporter; and
wherein the detecting is performed by an optical detector.

3. The method of claim 2, wherein the change in fluorescence is a decrease in fluorescence.

4. The method of claim 1, wherein the chemical reporter comprises a fluorescent reporter.

5. The method of claim 1, further comprising:
preparing the protonated PQP.

6. The method of claim 5, wherein preparing the protonated PQP comprises combining PQP and a non-volatile acid.

7. The method of claim 6, wherein the non-volatile acid comprises one or more of a carboxylic acid, a carboxylic acid containing polymer, or a sulfonic acid containing polymer.

8. The method of claim 7, wherein:
the carboxylic acid comprises one or more of hexacosanoic acid or stearic acid;
the carboxylic acid containing polymer comprises one or more of polyacrylic acid or polymethacrylic acid; or
the sulfonic acid containing polymer comprises polystyrenesulfonic acid.

9. The method of claim 1, wherein the amine compound comprises one or more of methamphetamine, methamphetamine hydrochloride, cocaine, cocaine hydrochloride, 3,4-methylenedioxymethamphetamine (MDMA), MDMA hydrochloride, heroin, or heroin hydrochloride.

10. The method of claim 1, wherein the chemical detector comprises a substrate reporter surface having a sensing channel comprising a plurality of chemical reporters disposed therein.

11. The method of claim 1, wherein the chemical detector comprises a substrate reporter surface having a flat surface comprising a plurality of chemical reporters disposed thereon.

12. A device comprising:
an inlet configured to receive the vapor-phase amine compound; and
the chemical detector comprising the chemical reporter configured to respond to the amine compound, wherein the protonated PQP comprises a combination of PQP and a non-volatile acid, and is configured to perform the method of claim 1 to detect a response of the chemical reporter to the amine compound to determine whether the amine compound is present.

13. The device of claim 12, further comprising:
an excitation source having an associated wavelength configured to illuminate the chemical reporter to provide the response as a change in fluorescence in the chemical reporter; and
wherein the chemical detector comprises an optical detector.

14. The device of claim 13, wherein the change in fluorescence is a decrease in fluorescence.

15. The device of claim 12, wherein the chemical reporter comprises a fluorescent reporter.

16. The device of claim 12, wherein the non-volatile acid comprises one or more of a carboxylic acid, a carboxylic acid containing polymer, or a sulfonic acid containing polymer.

17. The device of claim 16, wherein:
the carboxylic acid comprises one or more of hexacosanoic acid or stearic acid;
the carboxylic acid containing polymer comprises one or more of polyacrylic acid or polymethacrylic acid; or
the sulfonic acid containing polymer comprises polystyrenesulfonic acid.

18. The device of claim 12, wherein the amine compound comprises one or more of methamphetamine, methamphetamine hydrochloride, cocaine, cocaine hydrochloride, 3,4-methylenedioxymethamphetamine (MDMA), MDMA hydrochloride, heroin, or heroin hydrochloride.

19. The device of claim 12, wherein the chemical detector comprises a substrate reporter surface having a sensing channel comprising a plurality of chemical reporters disposed therein.

20. The device of claim 12, wherein the chemical detector comprises a substrate reporter surface having a flat surface comprising a plurality of chemical reporters disposed thereon.

* * * * *

UNITED STATES PATENT AND TRADEMARK OFFICE
CERTIFICATE OF CORRECTION

PATENT NO. : 10,830,764 B2
APPLICATION NO. : 15/842451
DATED : November 10, 2020
INVENTOR(S) : Lara B. Wald and Steven L. Keen Page 1 of 1

It is certified that error appears in the above-identified patent and that said Letters Patent is hereby corrected as shown below:

In the Specification

In Column 1, Line 34, change "Calorimetric" to --Colorimetric--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*